United States Patent [19]

Chiasson

[11] 4,297,509

[45] Oct. 27, 1981

[54] PROCESS FOR PREPARING ALKALI METAL SALTS 3-AMINO-2, 5-DICHLOROBENZOIC ACID

[75] Inventor: Bertrand A. Chiasson, South Charleston, W. Va.

[73] Assignee: Union Carbide Corporation, New York, N.Y.

[21] Appl. No.: 133,787

[22] Filed: Mar. 25, 1980

[51] Int. Cl.$^3$ ............................................. C07C 51/347
[52] U.S. Cl. ................................................... 562/456
[58] Field of Search ........................ 362/456; 260/580

[56] References Cited

U.S. PATENT DOCUMENTS

| | | | |
|---|---|---|---|
| 3,067,253 | 12/1962 | Dietzler et al. | 562/456 |
| 3,255,248 | 6/1966 | Corr et al. | 260/563 |
| 3,414,399 | 12/1968 | Weil et al. | 562/456 |
| 3,666,813 | 5/1972 | Hindin et al. | 562/456 |
| 3,910,995 | 10/1975 | Gelfand | 562/438 |
| 3,997,478 | 12/1966 | Petro | 252/470 |
| 4,059,627 | 11/1977 | Kritzler et al. | 562/456 |
| 4,070,401 | 1/1978 | Hirai et al. | 562/456 |
| 4,153,578 | 5/1979 | De Thomas et al. | 252/438 |

OTHER PUBLICATIONS

Paul, Bull Chim. Soc. Fr., vol. 13, pp. 208–211 (1946).

*Primary Examiner*—Natalie Trousof
*Assistant Examiner*—James H. Reamer
*Attorney, Agent, or Firm*—Dale Lynn Carlson

[57] ABSTRACT

This invention relates to a process of preparing alkali metal salts of 3-amino-2,5-dichlorobenzoic acid by the catalytic hydrogenation of alkali metal salts of 3-nitro-2,5-dichlorobenzoic acid in the presence of molybdenum-promoted Raney nickel catalyst.

8 Claims, No Drawings

PROCESS FOR PREPARING ALKALI METAL SALTS 3-AMINO-2, 5-DICHLOROBENZOIC ACID

FIELD OF THE INVENTION

This invention relates generally to 3-amino-2,5-dichlorobenzoic acid and more particularly, to an improved process for the production of alkali metal salts of 3-amino-2,5-dichlorobenzoic acid.

BACKGROUND OF THE INVENTION 3-amino-2,5-dichlorobenzoic acid and its alkali metal salts are well known in the art as important selective herbicides. The herbicidal activity of 3-amino-2,5-dichlorobenzoic acid, its functional derivatives and their preparation from the 3-nitro compounds are described in U.S. Pat. Nos. 3,014,063 and 3,174,841. The alkali metal salt is preferred since it is a water-soluble form of 3-amino-2,5-dichlorobenzoic acid which can be produced as a dry powder, thereby permitting reduction in packaging and shipping costs. It is known that the alkali metal salt of 3-amino-2,5-dichlorobenzoic acid can be prepared by reacting 3-amino-2,5-dichlorobenzoic acid with alkali metal base, or by reacting the amine salt of the acid (which cannot easily be produced free of water) with sodium hydroxide and removing the liberated amine from solution.

It is also known that the sodium salt of 3-amino-2,5-dichlorobenzoic acid can be prepared by the reduction of the sodium salt of 3-amino-2,5-dichlorobenzoic acid with hydrogen in the presence of Raney nickel catalyst. By way of illustration, such a reduction is described in U.S. Pat. No. 3,910,995.

The reduction process described in the above patent provides the sodium salt of 3-amino-2,5-dichlorobenzoic acid in relatively low yield. Consequently, there exists a need for more effective process for preparing the alkali metal salt of 3-amino-2,5-dichlorobenzoic acid in increased yield that avoids the need to resort to elaborate and cumbersome purification techniques.

SUMMARY OF THE INVENTION

According to the present invention, there is provided an improved method for preparing the alkali metal salt of 3-amino-2,5-dichlorobenzoic acid in high purity and yield by the reduction of the alkali metal salt of 3-nitro-2,5-dichlorobenzoic acid with hydrogen in the presence of molybdenum-promoted Raney nickel catalyst.

DETAILED DESCRIPTION OF THE PREFERRED EMBODIMENTS

The molar amount of the reactants can vary over a wide range. Preferably, the hydrogen is present in an amount sufficient to provide an amount of at least 3 moles per mole of the alkali metal salt of 3-nitro-2,5-dichlorobenzoic acid reactant. The hydrogen is preferably supplied to the reactor continuously under pressure, at the pressures specified below and, therefore, an excess of hydrogen will generally be present in the latter stages of the reaction.

As used herein, the term "molybdenum promoted Raney nickel catalyst" is used to encompass any molybdenum promoted activated nickel catalyst. Generally, these catalysts are produced by treating powdered nickel-aluminum-molybdenum alloys in a strong alkaline solution whereby the aluminum is removed from the alloy particles leaving as the residue porous particles of nickel-molybdenum. These catalysts can be produced in accordance with the method given in U.S. Pat. No. 2,948,687, incorporated herein by reference. The amount of molybdenum in the catalyst is preferably up to about 12 weight percent (more preferably from about 2 to about 12 weight percent) based on the total weight of the catalyst.

Since the alkali metal salt of 3-nitro-2,5-dichlorobenzoic acid is water-soluble, the reaction in accordance with the process of this invention can be suitably conducted in the presence of a water solvent. Although not preferred, any conventional organic solvent that does not interfere with the present reaction can alternatively be used, such as, for example, ethanol or methanol. The amount of solvent is not critical.

Any alkali metal salt of 3-nitro-2,5-dichlorobenzoic acid can be used in the process of the invention such as, for example, sodium, potassium, lithium, calcium and magnesium. Preferably, the sodium or potassium salt is employed.

The reaction temperature can vary over a wide range of from about 25° C. to about 125° C., preferably from about 85° C. to about 125° C.

The process of the invention is conducted in an enclosed reactor at superatmospheric pressure. Preferably, the hydrogen pressure in the reactor is maintained at between about 100 and about 800 psi, more preferably from about 400 to about 800 psi.

The reaction time is not critical and can vary from a few minutes to a day or more depending upon reaction conditions (temperature, pressure, pH, etc.) The reaction time is preferably between about 30 and 90 minutes.

The reaction pH is preferably maintained between about 6 and about 12. Adjustment of pH can be made using a suitable base such as sodium or potassium hydroxide in an amount effective in raising the pH to the above range.

The process of the present invention will generally provide the alkali metal salt of 3-amino-2,5-dichlorobenzoic acid in high purity and yield. If further purification is desired, however, it can be made by conventional means such as fractional recrystallaztion, liquid-liquid extraction and sublimation.

The following examples are intended to illustrate, but in no way limit, the present invention.

EXAMPLE 1

A solution was prepared by dissolving 100.0 grams of 98 wt. % 3-nitro-2,5-dichlorobenzoic acid in a mixture of 4 N sodium hydroxide and distilled water to give 1000 ml. of solution having a pH of 7.0. The solution was charged into a 2-liter stirred pressure reactor along with 6.08 grams of molybdenum-promoted Raney nickel, containing about 10 wt. percent molybdenum based on the total weight of the catalyst. The reactor was then closed, flushed with hydrogen, and heated to 95° C. When the temperature reached 95° C., the pressure inside the reactor was adjusted to 600 psi by the addition of hydrogen from a pressurized tank, and the stirrer was turned on. The pressure inside the reactor was maintained at 600 psi by intermittently adding hydrogen from the tank. When hydrogen uptake stopped after a reaction time of 80 minutes, the reactor was cooled to room temperature, vented, and opened. The catalyst was then filtered from the product solution, and the pH was raised from 4.09 to 7.09 by the addition of 11.9 ml. of 2 N aqueous sodium hydroxide. A portion of the product solution was evaporated to give a dry solid which, when analyzed by liquid chromatagraphy, was found to contain 93 wt. % of the sodium salt of 3-amino-2,5-dichlorobenzoic acid. This represents a yield of 95 percent based on the 3-nitro-2,5-dichlorobenzoic acid reactant.

COMPARATIVE EXAMPLE A

A solution was prepared by dissolving 100.0 grams of 98 wt. % 3-nitro-2,5-dichlorobenzoic acid in a mixture of 4 N sodium hydroxide and distilled water to give 1000 ml. of solution having a pH of 7. This solution was charged into a 2-liter stirred pressure reactor along with 6.18 grams of Raney nickel. The reactor was then closed, flushed with hydrogen, and heated to 95° C. When the temperature reached 95° C., the pressure inside the reactor was adjusted to 600 psi by the addition of hydrogen from a pressurized tank, and the stirrer was turned on. The pressure inside the reactor was maintained at 600 psi by intermittently adding hydrogen from the tank. When hydrogen uptake stopped after a reaction time of 100 minutes, the reactor was cooled to room temperature, vented and opened. The catalyst was then filtered from the product solution, and the pH was raised from 4.82 to 7.2 by the addition of 2.0 ml. of 2 N aqueous sodium hydroxide. A portion of the product solution was evaporated to give a dry solid which, when analyzed by liquid chromatography, was found to contain 59 wt. % of the sodium salt of 3-amino-2,5-dichlorobenzoic acid. This represents a yield of 61 percent based on the 3-nitro-2,5-dichlorobenzoic acid reactant.

The results as given above indicate that a comparison employing Raney nickel catalyst (Comparative Example A) provided a relatively low yield of 59 percent as compared to an example employing the molybdenum-promoted Raney nickel catalyst of the present invention (Example 1) which provided a yield of 95 percent.

EXAMPLES 2 TO 10

Several additional examples (Examples 2 to 10) were run using molybdenum-promoted Raney nickel catalyst in accordance with the procedure of Example 1 and using reactants identical in kinds to those of Example 1. The reaction conditions and catalyst loadings (in wt. percent based on the weight of 3-nitro-2,5-dichlorobenzoic acid reactant) are given in Table I.

The results are given in Table I which follows. These results show that the process of the present invention is effective over a wide range of reaction conditions in producing product in high yield.

TABLE I

| Ex. # | Reaction Conditions | | | | | Reaction Time (Minutes) | Product[2] Yield (wt. %) |
|---|---|---|---|---|---|---|---|
| | Temperature (°C.) | Pressure (psi) | Catalyst Loading (wt. %) | Substrate Concentration[1] (wt. %) | pH | | |
| 2 | 75 | 250 | 5.2 | 2 | 5.9 | 165 | 95 |
| 3 | 85 | 400 | 6 | 8 | 12 | 70 | 92 |
| 4 | 95 | 600 | 6 | 50 | 7 | 60 | 95 |
| 5 | 85 | 800 | 6 | 20 | 7 | 35 | 95 |
| 6 | 85 | 800 | 6 | 30 | 9 | 55 | 95 |
| 7 | 95 | 800 | 6 | 30 | 9 | 55 | 95 |
| 8 | 95 | 600 | 20 | 5 | 7 | 22 | 91 |
| 10 | 30–95 | 600 | 6 | 20 | 7 | 310 | 94 |

[1]"Substrate concentration" denotes wt. percent of the sodium salt of 3-nitro-2,5-dichlorobenzoic acid based on the weight of the reaction mixture.
[2]"Product Yield" is given in wt. percent based upon the weight of the sodium salt of 3-nitro-2,5-dichlorobenzoic acid reactant.

What is claimed is:

1. A process for producing alkali metal salt of 3-amino-2,5-dichlorobenzoic acid in high yield comprising reacting alkali metal salt of 3-nitro-2,5-dichlorobenzoic acid with hydrogen under pressure at an elevated temperature in the presence of a molybdenum-promoted Raney nickel catalyst, said reaction being effected at a pH between about 6 and 12, and said reaction being effected in the presence of a water solvent.

2. The process of claim 1 wherein the alkali metal salt of 3-nitro-2,5-dichlorobenzoic acid is selected from the group consisting of sodium, potassium, lithium, calcium, magnesium salts, and mixtures thereof.

3. The process of claim 1 wherein said hydrogen is present in an amount sufficient to provide an amount of at least 3 moles per mole of the alkali metal salt of said 3-nitro-2,5-dichlorobenzoic acid.

4. The process of claim 1 wherein said elevated temperature is between about 25° C. and about 125° C.

5. The process of claim 4 wherein said elevated temperature is between about 85° C. and about 125° C.

6. The process of claim 1 wherein said pressure is between about 100 and 800 psi.

7. The process of claim 6 wherein said pressure is between about 400 and about 800 psi.

8. The process of claim 1 wherein said high yield of alkali metal salt of 3-amino-2,5-dichlorobenzoic acid is at least 90 percent, based on the amount of alkali metal salt of 3-nitro-2,5-dichlorobenzoic acid.

* * * * *